US006306654B1

(12) United States Patent
Boime et al.

(10) Patent No.: US 6,306,654 B1
(45) Date of Patent: Oct. 23, 2001

(54) FOLLICLE STIMULATING HORMONE-GLYCOSYLATION ANALOGS

(75) Inventors: Irving Boime; Martin M. Matzuk; Jeffrey L. Keene, all of St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 08/155,102

(22) Filed: Nov. 19, 1993

Related U.S. Application Data (63) Continuation of application No. 07/313,646, filed on Feb. 21, 1989, now abandoned.

(51) Int. Cl.⁷ .............................. C12N 15/06; C12N 15/16
(52) U.S. Cl. ...................... 435/360; 536/23.1; 536/23.5; 536/23.51; 435/320.1; 435/69.1; 435/69.4; 435/252.3; 435/252.33; 435/70.1; 435/91.1; 435/91.4; 435/360; 435/440; 435/455; 435/466; 435/91.42; 435/325; 435/351; 435/358
(58) Field of Search ............................ 435/320.1, 317.1, 435/69.1, 69.4, 240.2, 252.3, 70.1, 91.1, 91.4, 91.42, 325, 351, 358, 360, 440, 455, 466; 536/23.11, 23.5, 23.51; 930/110; 935/9, 10, 13, 22, 32, 70, 71; 530/397, 398

(56) References Cited

U.S. PATENT DOCUMENTS

| 4,840,896 | * | 6/1989 | Riddy et al. ......................... 435/69.4 |
| 4,959,455 | * | 9/1990 | Clark et al. ............................ 530/351 |

FOREIGN PATENT DOCUMENTS

| 8604589 | 8/1986 | (WO) . |
| WO 93/06844 | 4/1993 | (WO) . |

OTHER PUBLICATIONS

Watson et al., 1987, in: *Molecular Biology of The Gene*. Fourth Edition Benjamin/Cummings Publ. Co. Inc, Menlo Park, CA. p. 313.*
Harris, T. J. R. 1987 Protein Engineering 1, 449–458.*
Bradshaw et al. (eds.). 1990 in: *Proteins: Form and Function*. Elsevier Trends Journals. Cambridge. pp. 21–22.*
Parsons et al. 1983. J. Biol. Chem. 258, 240–244.*
Wallace et al. 1981. Nuc. Acids Res. 9, 3647–3656.*
Winter et al. 1982. Nature 299, 756–758.*
Haltiner et al. 1985. Nuc. Acids Res. 13, 1015–1025.*
Shortle et al. 1982. Proc. Natl. Acad. Sci USA, 79, 1588–1592.*
Troalen et al. 1988 J. Biol. Chem. 263, 10370–10376.*
Merz. et al. 1979 Hoppe–Seyleiz Z. Physiol. Chem. 360, 1783–1797.*

Bielinska et al. 1987. Biochem. Biophys. Res. Commun. 148, 1446–1452.*
Case, J.F. 1979. in: *Biology*. Second Edition. Macmillan Publ. Co. Inc., New York. p. 455.*
Baker et al. 1982, in: *The Study of Biology*, Fourth Edition. Addison Wesley Publ. Co. MA. pp. 417–419.*
Matzuk et al. 1987. Proc. Nat'l. Acad. Sci. USA 84:6354–6358.*
Boime, I. et al. "Structure–function studies of gonadotropins using site–directed mutagenesis and gene transfer: design of a long–acting follitropin agonist," *Chemical Abstracts* 123(1):347–356.
Fares, F.A. et al., "Design of a long–acting follitropin agonist by fusing the C–terminal sequence of the chorionic gonadotropin beta subunit to the follitropin bta subunit" *Proc. Natl. Acad. Sci. USA* 89(10):4304–4308, May, 1992.
Boorstein et al., *Nature* (1982) 300:419–422.
Boothby et al., *J. Biol. Chem.* (1981) 256:5121–5227.
Channing et al., *Endocrinol.* (1978) 103:341–348.
Fiddes et al., *J. Mol. Appl. Genetics* (1981) 1:3–18.
Fiddes et al., *Nature* (1980) 286:684–687.
Glaser et al., *Nature* (1986) 321:882–887.
Hayashizaki et al., *FEBS Letters* (1985) 188:394–400.
Jameson et al., *Mol. Endocrinol.* (1988) 2:806–815.
Jameson et al., *J. Clin. Endocrinol. Metab.* (1986) 64:319–327.
Kalyan et al., *J. Biol. Chem.* (1983) 258:67–74.
Keutmann et al., *Biochem.* (1983) 3067–3072.
Kim et al., *DNA* (1988) 7:277–333.
Matzuk et al., *Proc. Natl. Acad. Sci.* USA (1987) 6354–6358 C82L May 16, 1991.
Maurer et al., *DNA* (1986) 5:363–369.
Morrell et al., *J. Biol. Chem.*(1971) 246:1461–1467.
Moyle et al., *J. Biol. Chem.* (1975) 250:9163–9169.
Policastro et al., *J. Biol. Chem* (1983) 258:11492–11499.
Watkins et al., *DNA* (1987) 6:205–212.
Whitfield et al., "Frontiers in Thyroidology" (1986) Medeiros–Nato et al., editiors, pp. 173–176, Plenum Press, New York.
Biome et al., *Adv. Exp. Med. Biol.* (1986) 205:267–280.
Gottlieb et al., *J. Biol. Chem.* (1975) 250(9):3303–3309.
Matzuk et al., *J. Cell Biol.* (1988) 106:1049–1059.
Matzuk et al., *J. Biol. Chem.* (1989) 264(5):2409–2414.
Matzuk et al., *Mol. Endocrinol.* (1988) 2(2):95–100.
Stanley "Molecular Cell Genetics: The Chinese Hamster Ovary Cell" Gottesman ed., J. Wiley & Sons Publisher, New York, (1985) pp. 745–772.

\* cited by examiner

*Primary Examiner*—Christopher S. F. Low
(74) *Attorney, Agent, or Firm*—Morrison & Foerster LLP (57) ABSTRACT

Recombinant materials are provided for the production of the α-glycoprotein hormone subunit. These muteins have utility as antagonists and in altering pharmacokinetic activity of these hormones.

7 Claims, 9 Drawing Sheets

FIG.1

D3 gcttcaggctagcattggtcatattaataccccaacaaatccacaaggtgttagttgcacatgattttg TATAAAA ggtga
actgagatttcattcagtct acagctcttgccaggcaaggcagccgaccacaggtgagtcttggcatctaccgttttcaa
gtg gtgacagctacttttgaaattacagatttgtcaggacatggaggacaaa..0.7 kb... ttcattgttgcttccc
                                                       EXON I ag accaggATGAAGACACTCCAGTTTTTCTCTTTCTGTTGCTGGAAAAGCAATCTGCTGCAATAGCTGTGAGCTGACC
       MetLysThrLeuGlnPhePhePheLeuPheCysCysTrpLysSerCysAsnSerCysGluLeuThr
       -18                                                              1
                          EXON II
AACATCACCATTGCAATAGAGAAGAAGAAGAATGTCTTTCTGCATAAGCATCAACACCACCACTTGGTGTGGCTACTGCTAC
AsnIleThrIleAlaIleGluLysGluGluCysArgPheCysIleSerIleAsnThrThrTrpCysAlaGlyTyrCysTyr
10                                  20                                  30

ACCAGG gtaggtaccatg...1.35 kb..aaataggaacttccacaataaccttaactctcttcttaaactcctc
ThrArg

FIG. 2A ag GATCTGGTGTATAAGGACCCAGGCCCAAAATCCAGAGAAAACATGTACCTTCAAGGAACTGGTATAGGAACACAGTG
   AspLeuValTyrLysAspProAlaArgProLysIleGlnLysThrCysThrPheLysGluLeuValTyrGluThrVal
                40                              50                              60
                                               EXON III

AGAGTGCCCGGCTGTGTCTCACCATGCAGATTCCTTGTATACATACCAGTGGCCACCAGTCACTGTGGCAAGTGTGAC
ArgValProGlyCysAlaHisHisAlaAspSerLeuTyrThrTyrProValAlaThrSerThrValThrCysLysCysAsp
              70                              80

AGGGACAGCACTGATTGTACTGTGGAGGCCTACTGCTCCTTTGTGAAATGAAAGAATAAagatcagtg
SerAspSerThrAspCysThrValArgGlyLeuGlyProSerTyrCysSerPheGlyGluMetLysGluTerm
              90                              100                             110 gacatttcaggccacatacccttgtcctgaaggaccaagatattcaaaaagtctgtgtgtgcaatgtgccaggggaca aaccactggatcaggggattcagactctactgatcccctggtctgcagagggaactctggaattgagagtgctgggg

.....0.55 kb..... aaattgtaattgggctgtgtggaaattagcctgcctctattcattacttaaacaaattgatcac atgctactaggctcctgcaactccttttgagataaagggaaaaaaaccaaactatctcaccctacctccctaggatcc
                                                                              H1

FOLLICLE STIMULATING HORMONE-GLYCOSYLATION ANALOGS

This application is a continuation of application Ser. No. 07/313,646, filed Feb. 21, 1989, now abandoned.

TECHNICAL FIELD

The invention relates to the production of follicle stimulating hormone (FSH) with altered glycosylation patterns and activities. In particular, it concerns production of recombinant FSH under conditions which regulate the glycosylation pattern of the protein.

BACKGROUND ART

Human FSH is used therapeutically to regulate various aspects of metabolism pertinent to reproduction in the human female. For example, FSH partially purified from urine is used clinically to stimulate follicular maturation in anovulatory women with anovulatory syndrome or luteal phase deficiency. It is also used in combination with luteinizing hormone (LH) to stimulate the development of ovarian follicles for in vitro fertilization. The role of FSH in the reproductive cycle is sufficiently well-known to permit this sort of therapeutic use, but difficulties have been encountered due, in part, to the heterogeneity of the preparation from native sources. This heterogeneity is due to variations in glycosylation pattern.

FSH is one member of a family of heterodimeric human glycoprotein hormones which have a common alpha subunit, but differ in their hormone-specific beta subunits. The family includes, besides FSH, luteinizing hormone (LH), thyrotropin or thyroid stimulating hormone (TSH), and human chorionic gonadotropin (CG). In all cases, the alpha subunit is a 92 amino acid glycoprotein with two canonical glycosylation sites at the asparagines located at positions 52 and 78. The beta subunits are also glycoproteins; in addition to the N-linked glycosylation exhibited by the beta chains of all four hormones, human CG contains four mucin-like O-linked oligosaccharides attached to a carboxy-terminal extension unique to this hormone. The relevance of the O-linked glycosylation is not, apparently, related to the secretion and assembly of the hormone (Matzuk, M. M. et al. *Proc Natl Acad Sci USA* (1987) 84:6354–6358).

Genomic and cDNA clones have been prepared corresponding to the human alpha chain (Boothby, M. et al. *J Biol Chem* (1981) 256:5121–5127; Fiddes, J. C. et al. *J Mol App Genet* (1981) 1:3–18). The cDNA and genomic sequences of the beta subunits of the remaining three members of the family have also been prepared: for CG, as disclosed by Fiddes, J. C. et al. *Nature* (1980) 286:684–687 and by Policastro, P. et al. *J Biol Chem* (1983) 258:11492–11499; for luteinizing hormone by Boorstein, W. R. et al. *Nature* (1982) 300:419–422; and for TSH by Hayashizaki, Y. et al. *FEBS Lett* (1985) 188:394–400 and by Whitfield, G. K. et al. in "Frontiers in Thyroidology", (1986) Medeiros-Nato, G. et al. (eds) pages 173–176, Plenum Press, NY. These DNA segments have been expressed recombinantly, and biologically active material has been produced.

Although genomic clones and isolates for human FSH-beta hve been prepared (Watkins, P. C. et al. *DNA* (1987) 6:205–212; Jameson, J. L. et al., *Mol Endocrinol* (1988) 2:806–815; Jameson, J. L. et al. *J Clin Endocrinol Metab* (1986) 64:319–327; Glaser, T. et al. *Nature* (1986) 321:882–887), human FSH beta has not been engineered to permit recombinant production of the hormone. (The bovine beta FSH gene has also been obtained as disclosed in Maurer, R. A. et al. *DNA* (1986) 5:363–369; Kim, K. E. et al. *DNA* (1988) 7:227–333.) As disclosed in the invention herein, recombinant production of this FSH hormone permits regulation of the glycosylation pattern and thereby greater predictability in the formulation of therapeutically useful material.

While it is now understood that the glycosylation pattern of a particular protein may have considerable relevance to its biological activity, the importance of this pattern has largely been overlooked in characterization of glycoproteins. Emphasis has been placed on the amino acid sequence as if this were the sole component of the glycoprotein. The reasons for this myopia are largely historic, but this almost exclusive focus on the peptide aspect is clearly in error. For example, it is well known in the case of human CG that desialylation causes the hormone to be cleared rapidly via the liver (Morell, A. G. et al. *J Biol Chem* (1971) 246:1461–1467). It is also known that removal of carbohydrate internal to the sialic acid residues or complete deglycosylation converts human CG into an antagonist which binds more tightly to receptor but shows decreased biological activity in vitro (Channing, C. P. et al. *Endocrinol* (1978) 103:341–348; Kalyan, N. J. et al. *J Biol Chem* (1983) 258:67–74; Keutmann, H. T. et al. *Biochemistry* (1983) 3067–3072; Moyle, W. R. et al. *J Biol Chem* (1975) 250:9163–9169). Other glycoproteins, such as, for example, tissue plasminogen activator, are also known to be altered in their degree of activity when the glycosylation pattern is changed. Therefore, it appears that in order to regulate the therapeutic function of the glycoprotein hormones, it may be necessary to control both the level and nature of glycosylation.

DISCLOSURE OF THE INVENTION

The invention provides recombinantly produced human FSH which offers the opportunity for control of glycosylation pattern both on the alpha and beta portions of the heterodimer. Such glycosylation control can be obtained through either the prudent selection of the recombinant eucaryotic host, including mutant eucaryotic hosts, or through alteration of glycosylation sites through, for example, site directed mutagenesis at the appropriate amino acid residues. In any event, the recombinant production of this hormone obviates the complex mixture of glycosylation patterns obtained when the hormone is isolated from native sources.

In one aspect, the invention is directed to expression systems capable, when transformed into a suitable host, of expressing the gene encoding the FSH beta subunit. In additional aspects, the invention is directed to recombinant hosts which have been transformed or transfected with this expression system, either singly, or in combination with an expression system capable of producing the alpha subunit. In other aspects, the invention is directed to the FSH beta monomers and FSH heterodimers of defined glycosylation pattern produced by the recombinant host cells.

In another aspect, the invention is directed to specific mutants of FSH or other hormones of this family with altered glycosylation patterns at the two glycosylation sites in the alpha subunit, or to alpha subunit variants containing alterations at the carboxy terminus which affect activity and to glycosylation or other variants of the FSH beta subunit. Thus, in another aspect, the invention is directed to expression systems for the alpha subunit which lack glycosylation sites at the asparagine at position 52 or position 78 or both, for the FSH beta subunit and its variants, and to recombinant host cells transfected with these expression systems. The cells may be transfected with a subunit expression system singly or in combination with an expression system for a suitable alpha or beta subunit. The invention is directed also to the mutant glycoproteins with altered glycosylation or activity patterns produced by these cells.

In other aspects, the invention is directed to pharmaceutical compositions containing the variants set forth above, and to methods to regulate reproductive metabolism in subjects by administration of these glycoproteins or their pharmaceutical compositions.

MODES OF CARRYING OUT THE INVENTION

Definitions

As used herein, human alpha subunit, and human FSH, LH, TSH, and CG beta subunits as well as the heterodimeric forms have in general their conventional definitions and refer to the proteins having the amino acid sequences known in the art per se, or allelic variants thereof, deliberately constructed muteins thereof maintaining the activity of the native protein regardless of the glycosylation pattern exhibited, or mutant forms thereof having at least 90% homology with the native forms. "Native" forms of these peptides are those which have the amino acid sequences isolated from human tissue, and have these known sequences per se, or their allelic variants. "Mutein" forms of these proteins are those which have deliberate alterations in amino acid sequence produced by, for example, site-specific mutagenesis or by other recombinant manipulations, or which are prepared synthetically. These alterations result in amino acid sequences wherein the biological activity of the subunit is retained and/or wherein the subunit has at least 90% homology with the native form. A particularly preferred mutein of FSH beta, for example, is that wherein the amino acid carboxy terminal peptide (CTP) of hCG is fused to the carboxy terminus of FSH beta. A preferred mutein of the alpha subunit for use in antagonists of the various heterodimers has alterations in the amino acids of positions 88–92.

Although it is recognized that glycosylation pattern has a profound influence on activity both qualitatively and quantitatively, for convenience the terms FSH, LH, TSH, and CG beta subunits refers to the amino acid sequence characteristic of the peptides, as does "alpha subunit". When only the beta chain is referred to, the terms will be, for example, FSH beta; when the heterodimer is referred to, the simple term "FSH" will be used. It will be clear from the context in what manner the glycosylation pattern is affected by, for example, recombinant expression host or alteration in the glycosylation sites. Forms of the glycoprotein with specified glycosylation patterns will be so noted.

A "transfected" recombinant host cell, i.e., a cell "transfected" with the recombinant expression systems of the invention, refers to a host cell which has been altered to contain this expression system by any convenient manner of introducing it, including transfection, viral infection, and so forth. "Transfected" refers to cells containing this expression system whether the system is integrated into the chromosome or is extrachromosomal. The "transfected" cells may either be stable with respect to inclusion of the expression system or not. In short, "transfected" recombinant host cells with the expression system of the invention refers to cells which include this expression system as a result of their manipulation to include it, when they natively do not, regardless of the manner of effecting this incorporation.

"Expression system" refers to a DNA sequence which includes a coding sequence to be expressed and those accompanying control DNA sequences necessary to effect the expression of the coding sequence. Typically, these controls include a promoter, termination regulating sequences, and, in some cases, an operator or other mechanism to regulate expression. The control sequences are those which are designed to be functional in a particular target recombinant host cell and therefore the host cell must be chosen so as to be compatible with the control sequences in the constructed expression system.

As used herein "cells", "cell cultures", and "cell lines" are used interchangeably without particular attention to nuances of meaning. Where the distinction between them is important, it will be clear from the context. Where any can be meant, all are intended to be included.

Isolation of the Gene Encoding FSH Beta

An important aspect of the present invention is the provision of an FSH beta-encoding DNA which is readily manipulated for insertion into expression systems. The gene, suitable for inclusion in expression systems intended for host cells capable of processing introns, was prepared as follows:

Genomic DNA from JAr choriocarcinoma cells (a human placental donor) was partially digested with MboI and cloned into the BamHI site of lambda MG3, a vector described Helms, C., et al. *DNA* (1985) 4:39–49; this vector is a derivative of lambda L47 which is described by Loenen, W. A. M., et al. *Gene* (1980) 10:249–259. The size of the inserts was typically 15–20 kb. Approximately $5\times10^5$ plaques were obtained and screened according to the method of Benton, W. D., et al. *Science* (1977) 196:180–182 using the 41 mer encoding amino acids 94–107 of exonIII of human FSH beta as described by Watkins, P. C., et al. *DNA* (1987) 6:205–212. This 41 mer has the sequence:

TGTACTGTGCGGGCCTGGGGCGGAGC-TACTGCTCCTTTGG.

Two positive clones were isolated by repeated plaque purification and shown by restriction analysis to be identical; furthermore, the PstI cleavage patterns were consistent with those obtained by Glaser, T. et al. *Nature* (1986) 321:882–887 (supra). Restriction fragments were subcloned into pUC18 for further restriction analysis and into M13 for sequencing by the dideoxy chain termination method of Sanger, F., *Proc Natl Acad Sci USA* (1977) 74:5463–5467. A 3.7 kb HindIII/BamHI fragment contained in the 16.5 kb insert of these clones contains the hFSH beta coding sequence.

Figure 1:
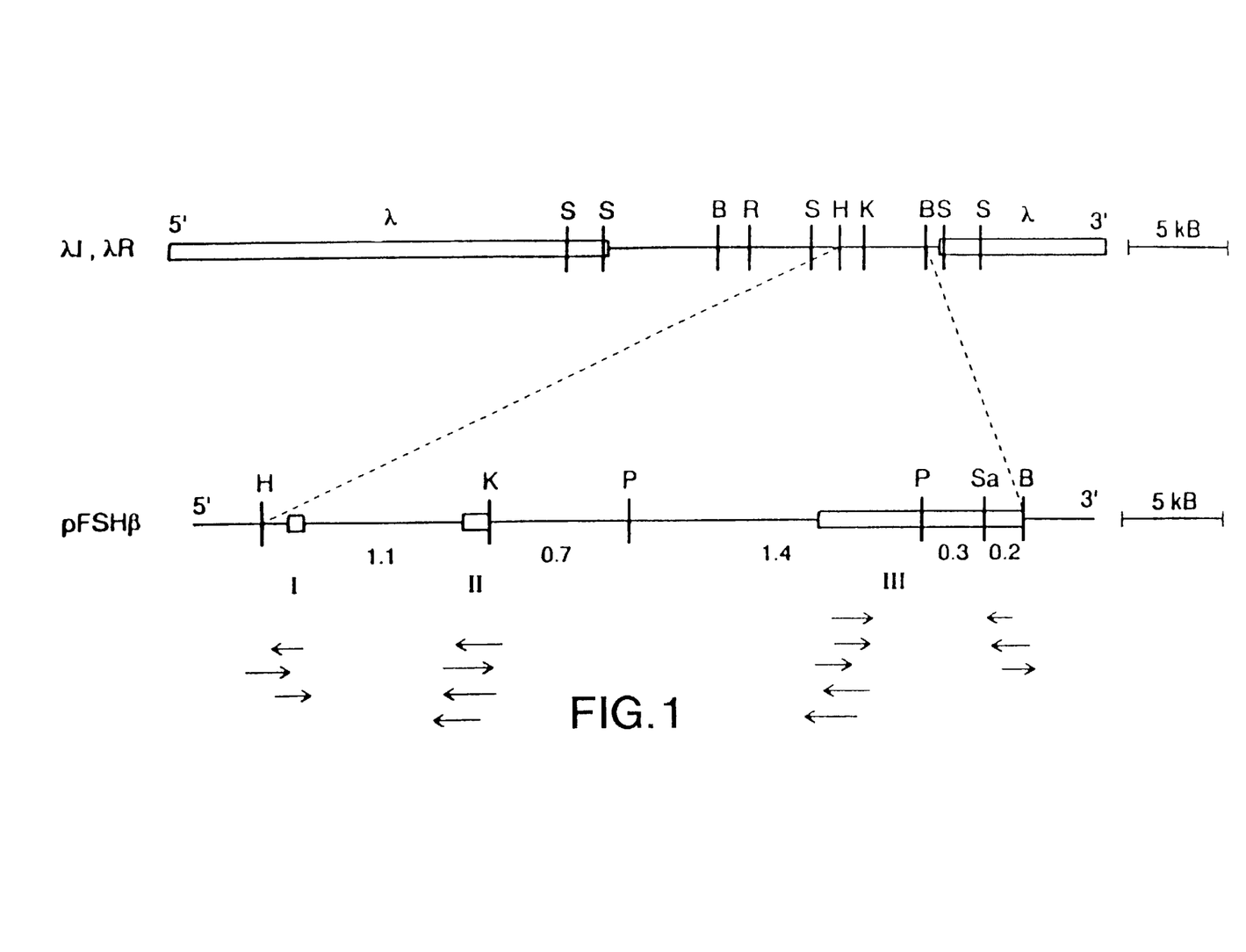
FIG. 1 shows a restriction enzyme map of the human FSH beta gene.

The clones were designated lambdaI and lambdaR, and have identical restriction maps and are approximately 16.5 kb in length. The restriction map of the full length clones are shown in FIG. 1, along with a restriction map of the 3.7 kb human FSH beta coding sequence.

Figure 2A:
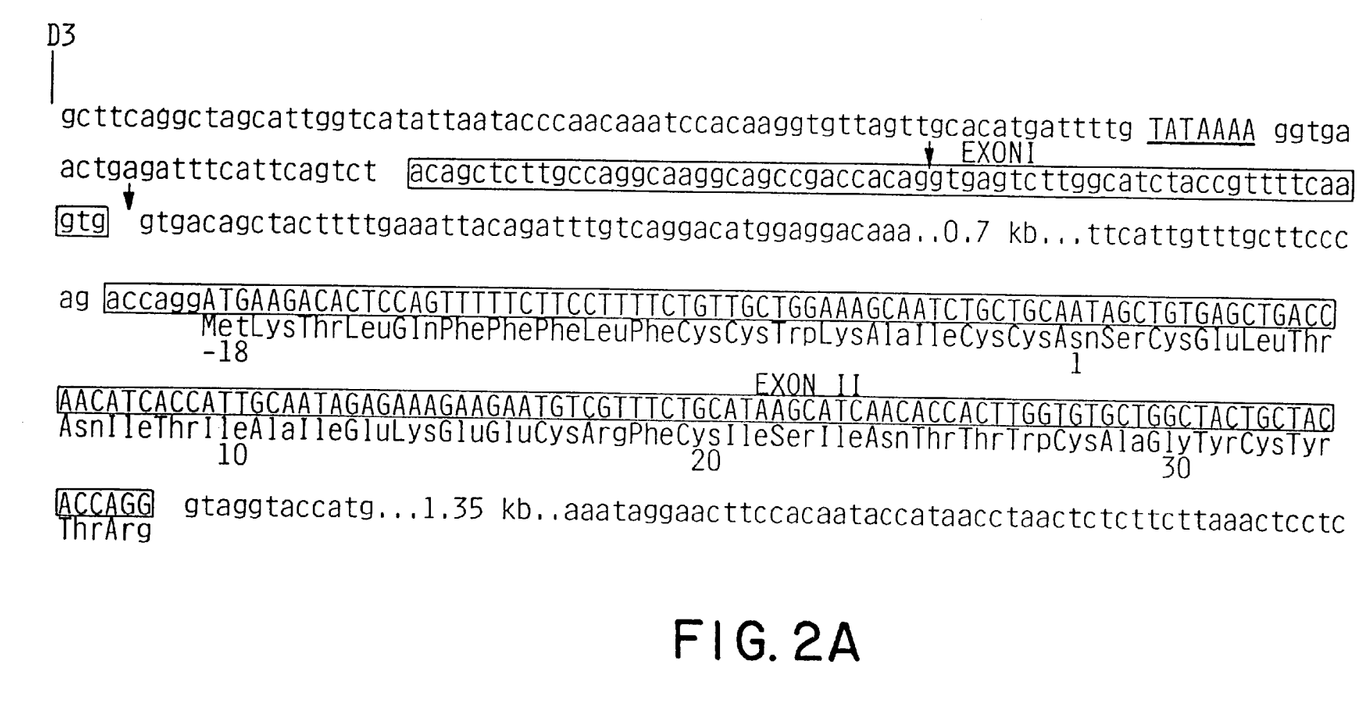
FIG. 2 shows the nucleotide sequence of the human FSH beta gene.
Figure 2B:
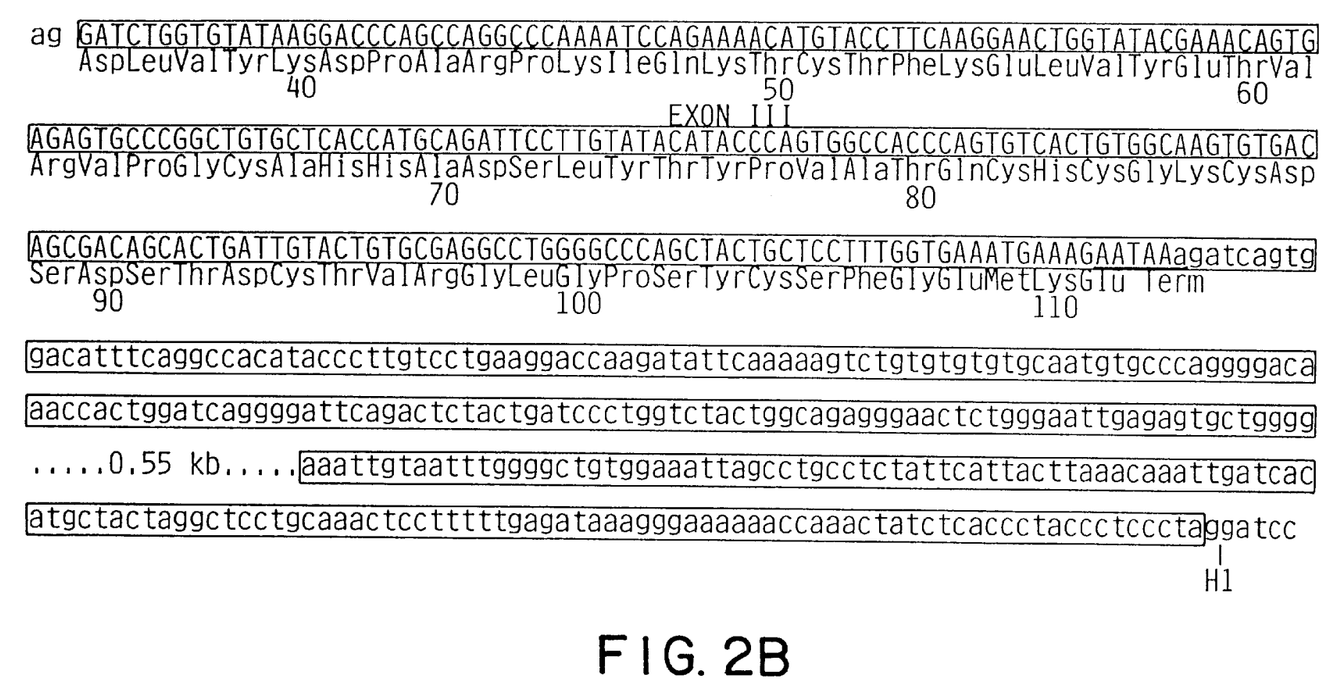

The results of sequencing the human FSH beta gene are shown in FIG. 2. As shown in FIG. 2, the coding sequence is divided into three exons. ExonI contains a 5' untranslated tract previously reported to encode two transcripts of either 33 or 63 bp (Jameson, J. L. et al. *Mol Endocrinol* (1988) 2:806–815). ExonII encodes an 18 amino acid signal peptide and amino acids 1–35 of the mature protein. ExonIII encodes amino acids 36–111 and about 1.1 kb of 3' untranslated sequence. ExonsI and II are separated by an intron of about 800 bp, and ExonsII and III by an intron of about 1.4 kb.

The nucleotide sequence obtained is similar to that reported by Watkins, T. C. et al. *DNA* (1987) 6:205–212 and Jameson, J. L. et al. (supra), except that tyrosine 58 is encoded by TAC rather than TAT and there are differences from Watkins in the 3' and 5' untranslated regions. A putative transcriptional start site 32 bp downstream from the TATA element is assigned by analogy to the bovine gene reported by Kim, K. E., et al., *DNA* (1988) 7:227–333. The sequence in FIG. 2 shows a single polyadenylation signal (AATAAA) overlapping the termination codon and recent evidence from the bovine gene (supra) and human clones (Jameson, J. L. et al., (supra)) indicates the presence of an approximately 1.1 kb 3' untranslated tract which may contain alternate polyadenylation signals.

The amino acid sequence shown in FIG. 2 is identical to that reported by that of Watkins (supra) but differs from that reported earlier by protein sequencing of purified human FSH beta. The carboxy terminal sequence Tyr-Pro-Thr-Ala-Leu-Ser-Tyr reported by Saxena, D. B., *J Biol Chem* (1976) 251:993–1005 is found neither in the sequence shown in FIG. 2 nor in the protein based sequence reported by Shome, B., et al., *J Clin Endocrinol Metab* (1974) 39:203–205. A more recent determination of the amino acid sequence confirms the sequence deduced from the DNA (Stone, B. et al. *J Prot Chem* (1988) 7:325–339.

Construction of Expression Vectors for Native Human Alpha Subunit and its Muteins It is understood in the art that N-linked glycosylation occurs at the tripeptide site Asn-X-Thr/Ser, two of which sites occur in the human alpha subunit, at Asn52 and Asn78. Site-directed mutagenesis was performed on a human alpha subunit fusion gene to alter these sites, wherein the fusion gene was constructed as follows:

The alpha subunit cDNA is obtained as described by Matzuk, M. M. et al. *J Cell Biol* (1988) 106:1049–1058 (supra) as a BamHI/XhoI framed nucleotide sequence containing an XbaI site in the coding sequence. A genomic fragment bounded by EcoRI and a XhoI site containing exons III and IV, with an XbaI site in exonIII was obtained from the human choriocarcinoma library. XbaI/XhoI digestion of both the genomic fragment and alpha subunit cDNA, followed by religation at the XbaI site creates the alpha subunit mini gene as a BamHI/XhoI fragment, containing a BglII site derived from the genomic fragment downstream of ExonIV. The BamHI/BglII fragment digested from the mini gene is used as the alpha subunit-encoding insert in the construction of expression vectors; the BamHI/XhoI fragment itself is ligated into M13 UM20 for site-directed mutagenesis.

For alteration of Asn52 and Asn78, respectively, the 22-mer oligomers GGTGACGTCCTTTTGCACCAAC and CTTAGTGGAGCGGGATATG respectively were used. This resulted in a substitution of aspartate residues for asparagine. Three mutants were constructed: αΔAsn-1 (position 52), αΔAsn-2 (position 78), and αΔAsn-1+2 (both positions). Corresponding changes were made by substituting the codon for alanine in place of that for threonine at positions 54 and 80 using the 26 mers: GTGGACTCTGAG-GCCACGTTCTTTTG and CAGTGGCACGCCGCATGGTTCTCCAC, respectively to obtain αΔ-Thr1, αΔThr2 and αΔThr(1+2).

Figure 7A:
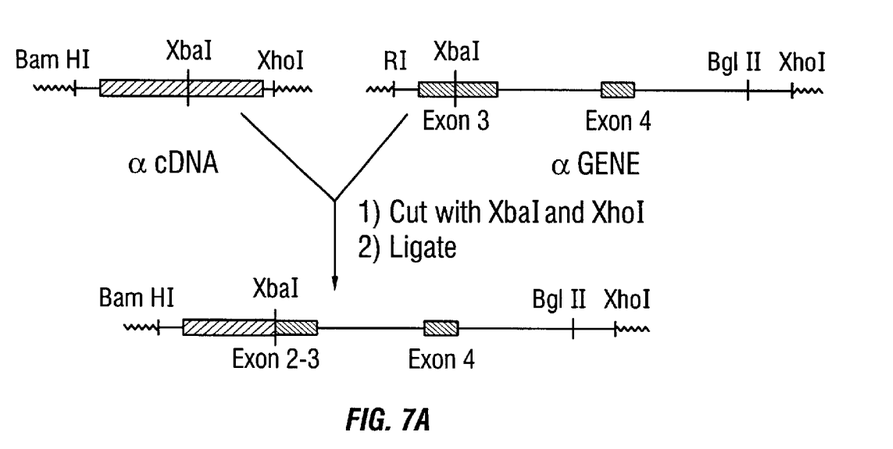
FIGS. 7A and 7B show the construction of expression vectors for the human alpha subunit.
Figure 7B:
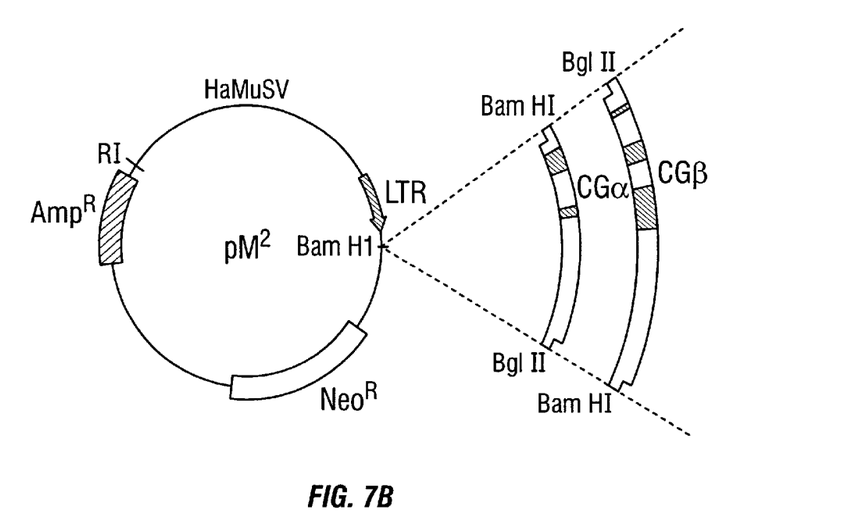

The wild type or mutant alpha subunits were then ligated into the host vector pM² as 2.4 kb mini genes using the BamHI/BglII fragments and were placed under control of the LTR promoter by insertion into the BamHI site downstream of the LTR. The construction of this expression vector having the human alpha sequence under control of LTR is shown in FIG. 7. The resulting vector shown, pM²/CGα is then used as the source of the human alpha expression unit in pM²/α by excising this unit as an EcoRI/EcoRI fragment and ligating it into the EcoRI site of pM² (Matzuk, M. M. et al. *Mol Endocrinol* (1988) 2:95–100) incorporated herein by reference.

In addition to muteins of the alpha subunit which have altered glycosylation patterns, a group of muteins with reduced or zero activity in signal transduction is also prepared. Experiments using chemical derivatization in in vitro assays indicate that amino acids at positions 88–92 (tyr-tyr-his-lys-ser) are necessary for the signal transduction activity of the hormone. Accordingly, deletion or alteration of one or more of these amino acids by site-directed mutagenesis results in analogs which continue to bind to receptor but have reduced or negligible activity. All four of the hormones sharing this alpha subunit can thus be prepared as antagonists for the relevant hormone.

Both the wild type and mutant vectors can be used as a source of human alpha subunit. Of particular importance are mutants of the alpha subunit in which the glycosylation site at Asn-52 is altered. Such mutated sequences when ligated into expression systems and transfected into appropriate host cells result in production of proteins which, when combined with the appropriate beta subunit have antagonist activity for the relevant hormone.

Construction of Expression Vectors for FSH Beta

Figure 3A:
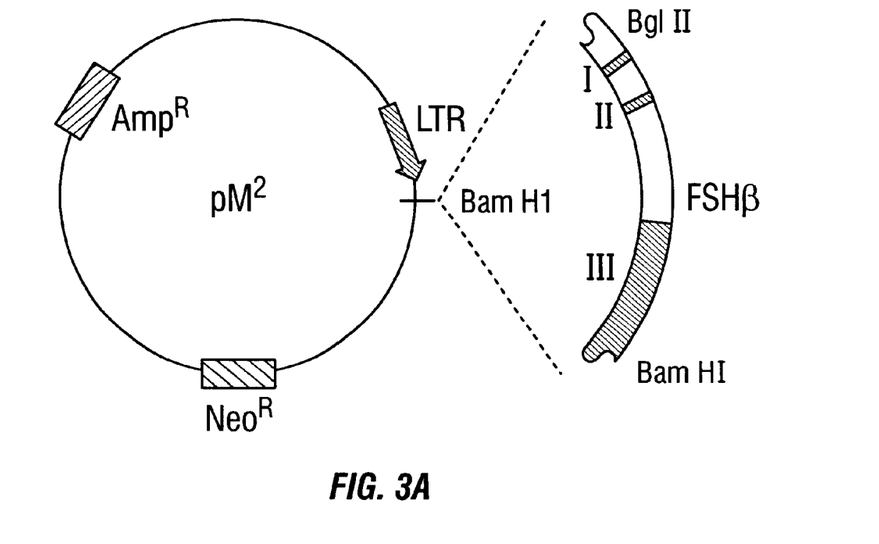
FIGS. 3A and 3B show expression vectors for production of human beta FSH.
Figure 3B:
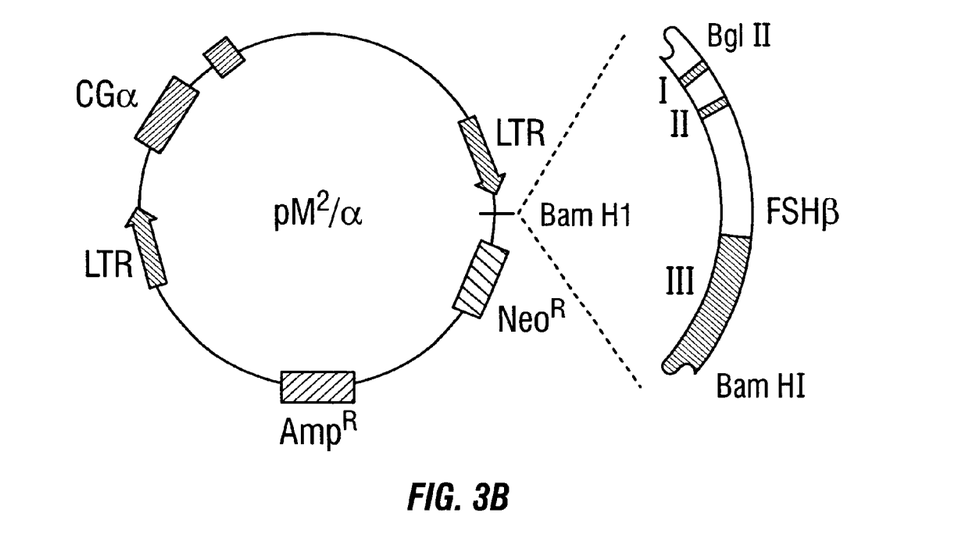

The construction of expression vectors for FSH beta alone and for both FSH beta and the human alpha subunit is shown in FIG. 3. The host vectors, pM² and pM²/α have been described previously. pM², as described by Matzuk, M. M. et al., *Proc Natl Acad Sci USA* (1987) 84:6354–6358, is a derivative of pSV2Neo and contains the ampicillin resistance gene (amp$^r$), the neomycin resistance gene (neo$^r$), and the Harvey murine sarcoma virus long terminal repeat (LTR) promoter with a unique downstream BamHI site. The vector is diagrammed in FIG. 3. pM²/α contains an alpha subunit mini gene downstream from a second LTR. The construction of pM²/α is described by Matzuk, M. M. et al. *Mol Endocrinol* (1988) 2:95–100 and the alpha subunit mini gene is described by Matzuk, M. M. et al. *J Cell Biol* (1988) 106:1049–1058, both incorporated herein by reference. This vector is also shown in FIG. 3.

For insertion of the inserted HindIII/BamHI fragment into either vector, the 5' HindIII site of FSH beta-containing pUC18 vector (pFSH beta), was converted to a BglII site using oligonucleotide linkers, and the modified pFSH beta vector digested with BglII and BamHI. The resulting 3.7 kb BglII/BamHI fragment was inserted into the unique BamHI site downstream of the LTR promoters in each vector, and orientation was confirmed by restriction analysis.

The foregoing constructions are, of course, merely illustrative of expression vectors or systems which can be constructed for the production of FSH beta or its muteins alone or of the corresponding heterodimeric hormone. Alternate control sequences can be ligated to the coding sequence of human FSH beta to effect expression in other eucaryotic cells which will provide suitable glycosylation. A variety of control sequences is known in the art, and methods to ligate the beta FSH coding sequence are of course also available. For example, suitable yeast promoters include promoters for synthesis of glycolytic enzymes including those for 3-phosphoglycerate kinase, or promoters from the enolase gene or the leu2 gene. Suitable mammalian promoters include the early and late promoters from SV40, or other viral promoters such as those derived from polyoma, adenovirus 2, bovine papilloma virus or avian sarcoma viruses. Suitable viral and mammalian enhancers can also be used. Expression in insect cells using a baculovirus promoter has also been reported. While less common, expression systems suitable for plant cells are also available.

A wide variety of expression vectors can be constructed utilizing various forms of the DNA encoding the desired amino acid sequence as shown in FIG. 2, or its alleles or modified (mutein) forms. The genomic DNA can be inserted directly into expression systems intended for eucaryotic host cells capable of processing introns. The nucleic acid sequences encoding the protein can be used directly from the genomic clone as described herein, or can be entirely or partially synthesized using standard solid phase oligonucleotide synthesis techniques as described, for example, by Nambiar, K. P. et al. *Science* (1984) 223:1299 or by Jaye, E. et al. *J Biol Chem* (1984) 259:6311. These techniques are now commercially available. It is evident, of course, that not only the specific nucleotide sequences shown in FIG. 2 can be employed, but also nucleotide sequences employing codons which are degenerate with those shown.

In addition to expression vectors capable of reducing native human FSH beta (i.e., that of the amino acid sequence shown in FIG. 2 or the allelic variants thereof), the corresponding vectors capable of expressing genes encoding muteins of FSH beta are also constructed.

One important mutein encoding sequence is obtained by ligating the DNA sequence encoding the carboxy terminal extension peptide of CG beta (CTP) to the 3' end of the FSH beta encoding sequence. To the C-terminal Glu of FSH beta at position 111 is ligated the downstream sequence of amino acid 112 to the carboxy terminus of CG beta, or a variant thereof. Preferred variants include those wherein the Ser at position 112 of CG beta is replaced by Ala. The extended form is conveniently obtained by ligation of HindIII-digested FSH beta encoding insert with the HindIII digest of CG beta cDNA. This religation results in the Ser →Ala substitution. The protein resulting from expression of this sequence when produced as the heterodimer FSH is expected to have the biological activity of native FSH but a prolonged circulating half-life. This expectation is made in view of the longer half-life of CG as compared to LH, which is possibly ascribable to the presence of a number of O-linked glycosylation sites in the CTP as described by Van Hall, E. *Endocrinol* (1971) 88:456. A major problem with FSH in clinical use is the relatively short circulating half-life of this protein (Wide, L. *Acta Endocrinol* (1986) 112:336).

Additional muteins of FSH beta are prepared by deleting or altering the N-linked glycosylation sites represented by the Asn-Thr combinations at positions 7/9 and 24/26 of the native sequence. The protein produced from expression of a system capable of expressing the genes encoding these muteins is expected to show adequate receptor binding with respect to the FSH beta receptor, and when heterodimerized with a suitable alpha subunit can be used as an antagonist for FSH activity; or, when heterodimerized with a normal alpha subunit can be used as an FSH substitute.

Production of Human FSH with Glycosylation Defined by Host Choice

The expression systems constructed according to the preceding paragraph can be employed to produce FSH beta either alone or in combination with the human alpha subunit, so that the protein obtained has a glycosylation pattern which is internally consistent within the sample and which is characteristic of the recombinant host employed, and optionally modified by changes in the glycosylation sites contained on the amino acid sequence. Recombinant hosts suitable to the expression system constructed must, of course, be employed.

With respect to the expression system illustrated in the above paragraph employing the Harvey murine sarcoma virus long terminal repeat, suitable host cells are mammalian, in particular, host cells which are derived from rodents. A particularly preferred host cell, because of convenience and consistency in glycosylation pattern, is a Chinese hamster ovary cell. For the illustrated expression systems, transfectants of CHO cells were obtained by transfection of CHO cells according to the procedure of Matzuk, M. M. et al. (1987), supra, except that the cells were maintained in alpha MEM containing 10% (v/v) bovine calf serum, 100 U/ml penicillin and 100 ug/ml streptomycin as a growth medium. Stable transfectants were selected from this growth medium supplemented with 250 ug/ml G418. Dimer-secreting clones (i.e., those derived from transfection with $pM^{2/}\alpha$ into which FSH beta had been inserted) were isolated by screening media and lysates with alpha and beta antisera. Cultures transfected with $pM^2$ into which FSH beta was inserted were screened by immunoprecipitation of lysates with FSH beta antisera.

Of course, the human alpha subunit can be expressed on a separate vector and, for example, $pM^{2/}\alpha$ or $pM^2CG\alpha$ can be cotransfected with the plasmid $pM^2FSH\beta$ into CHO cells for synthesis of the dimeric hormone.

The expression systems described above for human FSH beta inserted into $pM^2$ for expression of FSH beta alone or into $pM^{2/}\alpha$ for expression in tandem with the alpha subunit were transfected into CHO cells and stable clones shown to express the beta subunit or dimer were continuously labeled with $^{35}$S-cysteine for 6 hr. The proteins secreted into the media and from cell lysates were immunoprecipitated with appropriate antisera and resolved on SDS-PAGE. The results are shown in FIG. 4 in comparison with the behavior of transformants expressing the gene for human CG beta.

Figure 4A:
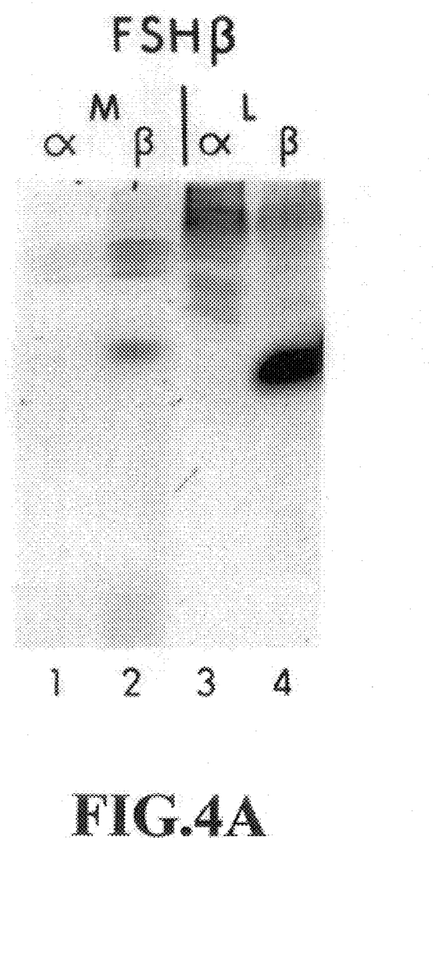
FIGS. 4 and 4 (cont.) show 35-S cysteine labeled FSH or FSH beta immunoprecipitated from cell lysates and media.
Figure 4B:
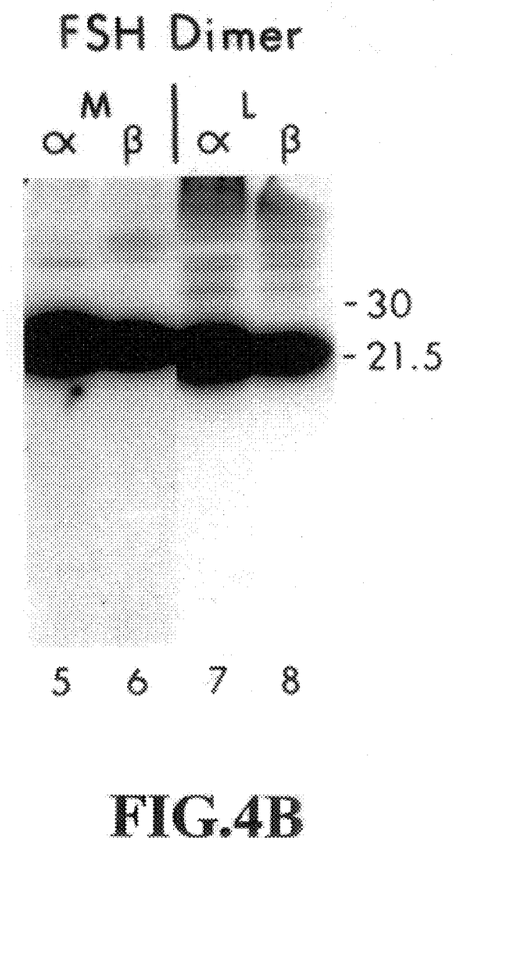
Figure 4C:
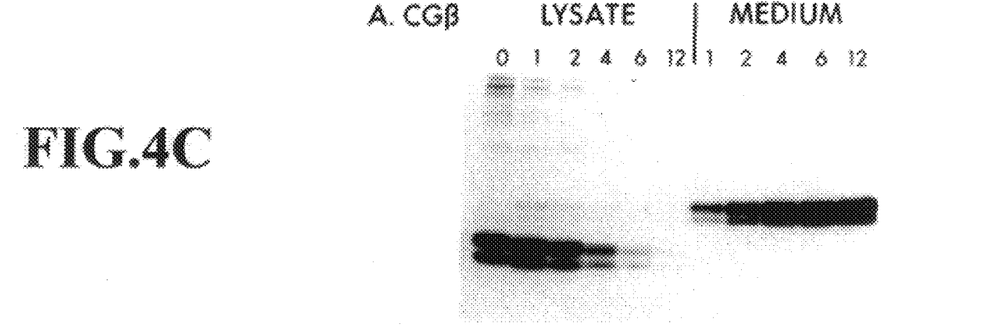

FIG. 4a, which displays gels from 6 hr labeling, shows that in the absence of the alpha subunit, FSH beta is retained in the lysate, while, as shown in FIG. 4b, when the alpha subunit is present, the dimer is formed and efficiently secreted into the medium. The results of experiments wherein the cells are pulse labeled with $^{35}$S-cysteine for 20 min and chased with unlabeled cysteine for up to 12 hr are shown in the remaining segments of FIG. 4. FIG. 4c shows the results for the beta subunit of CG where the lower molecular weight beta subunit in the medium is apparently due to the differences in the extent of glycosylation at the 2 Asn-linked glycosylation sites on CG beta and is unique to this beta subunit. The half-life of CG beta from lysates and of appearance of CG beta in the medium are identical at about 2 hr and almost all the secreted beta subunit can be recovered.

Figure 4D:
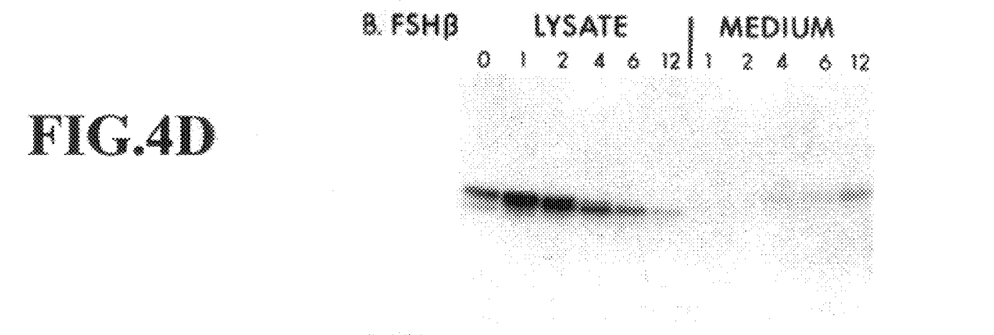
Figure 4E:
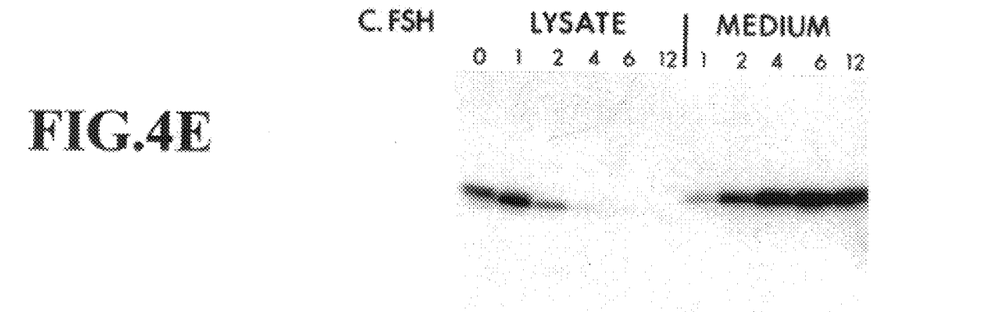

FIG. 4d shows that FSH beta alone is secreted much less efficiently and as does CG beta, disappears from the cell lysates after about 5 hr; less than 20% is recovered in the medium after 12 hr. Similarly to the beta subunits of LH and TSH, FSH beta alone is inefficiently secreted and slowly degraded intracellularly. However, FIG. 4e shows that the presence of the alpha subunit stabilizes and enhances the secretion of the beta subunit for FSH. The half-life for disappearance from the lysates was about 90 min, and 90% was recovered in the medium after 12 hr. This behavior is similar to that shown for TSH above, but different from both CG and LH.

Figure 5A:
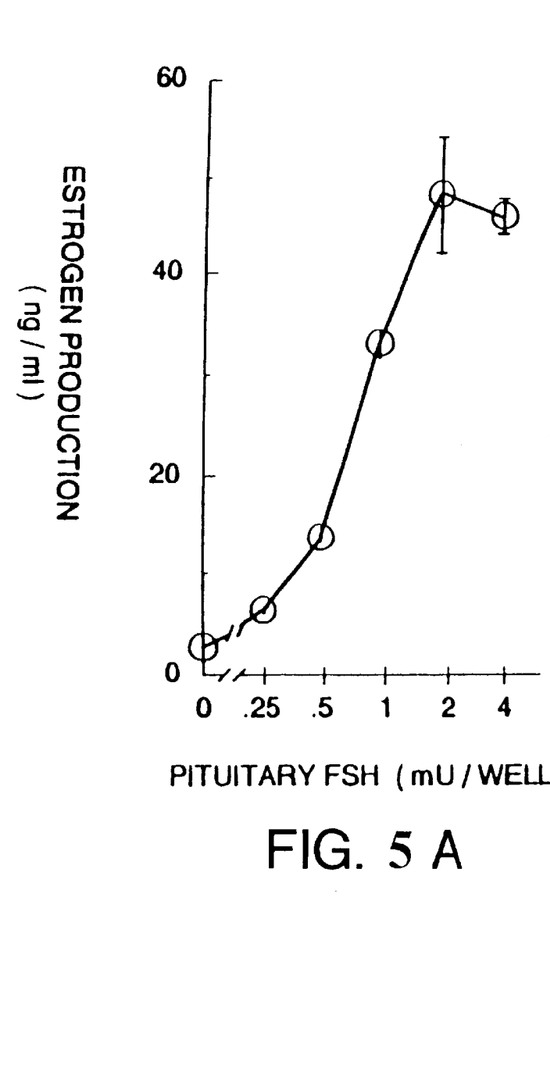
FIG. 5 shows the bioassay of recombinant human FSH.
Figure 5B:
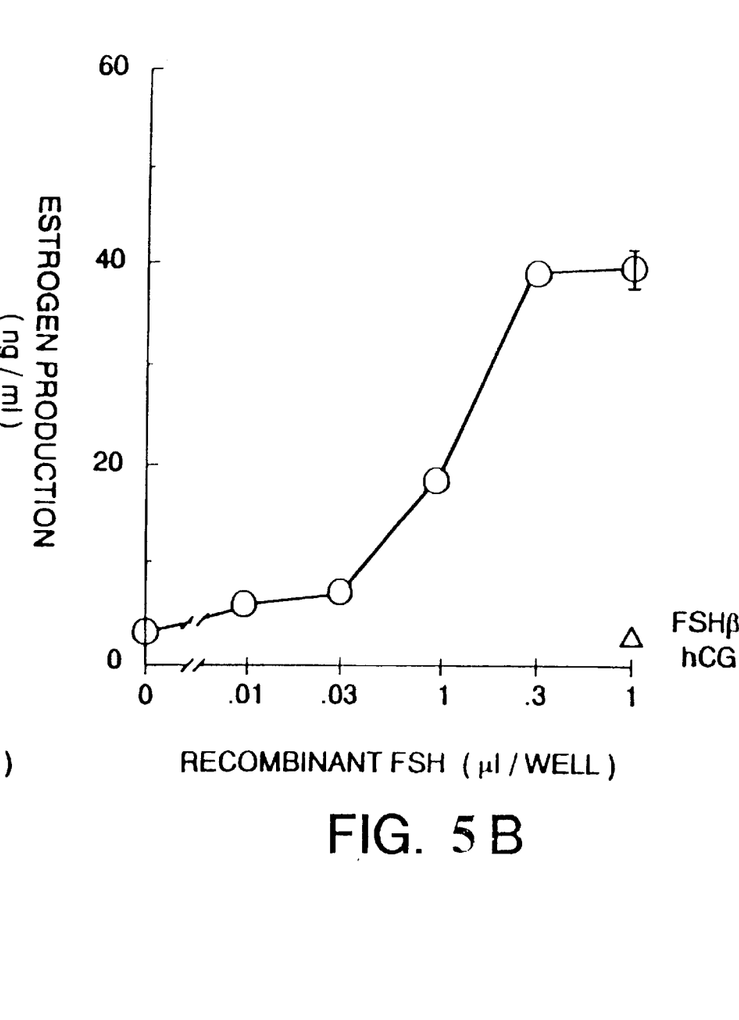

The transformants secreting dimer were tested for biological activity and by chromatofocusing. Rat granulosa cells were treated with increasing aliquots (0.01–1.0 ul/ml) of recombinant FSH-containing medium in an in vitro assay for steroidogenesis as described by Jia, X. C., et al. *J Clin Endocrinol Metab* (1986) 621243–1249; Jia, X. C. *Endocrinol* (1986) 119:1570–1577. The results of this assay are shown in FIG. 5. These results show that maximum estrogen production was 10-fold higher than basal values and similar to that induced by pituitary FSH standard LER-907. Neither recombinant CG nor purified FSH beta alone stimulate estrogen production. The results show that the biologically active FSH dimer is secreted at about $1.1\pm0.4$ IU/$10^6$ cells/ 24 hr corresponding to a specific activity of 6600 IU/mg immunoreactive FSH. The cells thus secrete 500 ng FSH/$10^6$ cells in 24 hr.

Figure 6A:
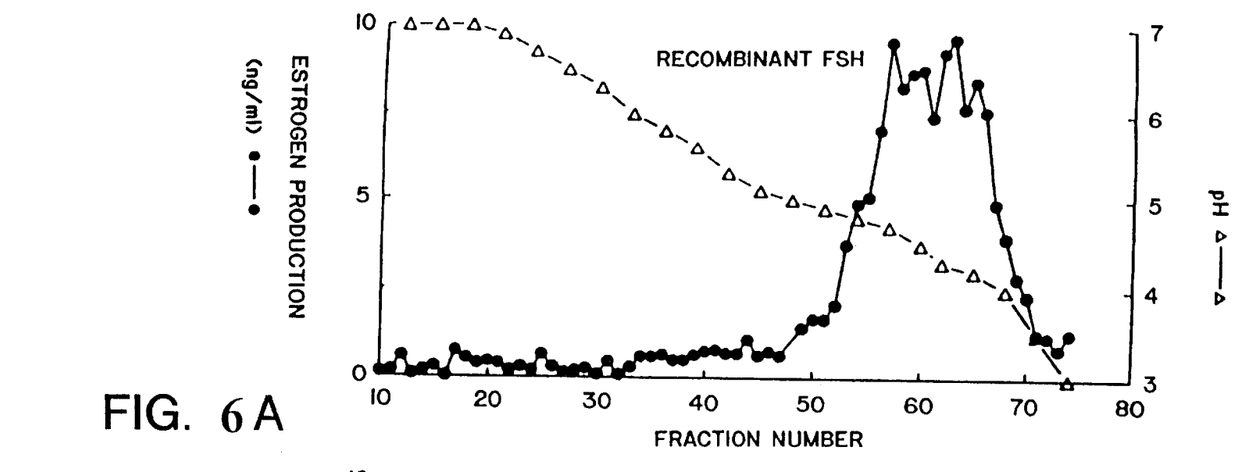
FIG. 6 shows chromatofocusing of recombinant and pituitary human FSH.
Figure 6B:
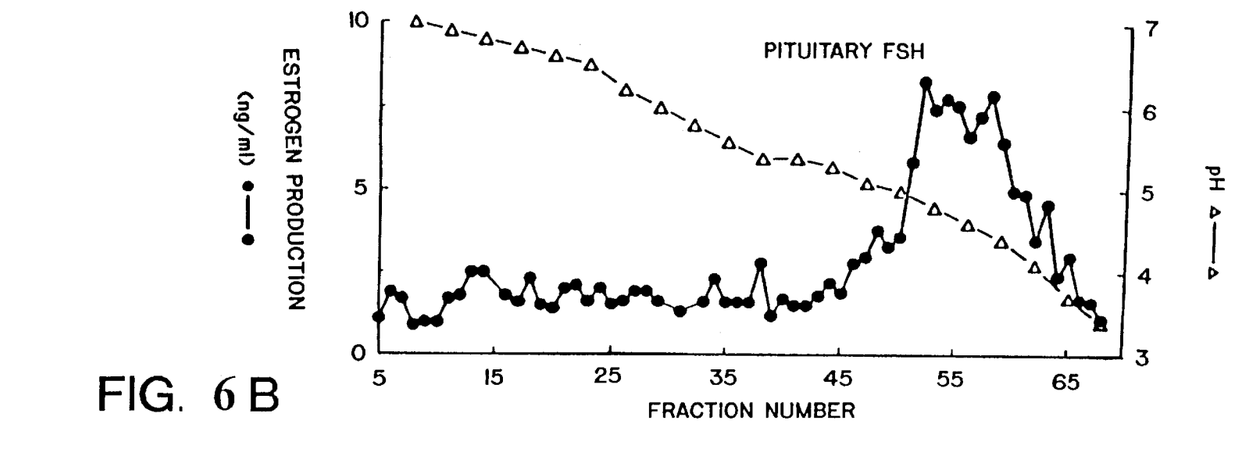

The medium from the transfected CHO cell cultures was chromatographed on a PBE-94 column with a pH gradient from 7.0–3.5 and the FSH bioactivity in each fraction was determined based on the in vitro assay described above. As a control, purified human FSH (NIADD-hFSH-1-3) was treated similarly. The results, shown in FIG. 6, indicate that both recombinant and isolated human FSH show one major peak of activity with pI values between 5.0–3.6 for recombinant FSH and between 5.2 and 3.6 for purified FSH. Pituitary FSH displayed a heterogeneous range of bioactive alkaline forms which was not seen in the recombinant protein. The results from chromatofocusing clearly indicate a uniform nonheterogeneous glycosylated form of the protein.

In a similar manner, vectors constructed with the wild type or mutant alpha subunit genes (see above) are constructed to obtain human FSH with glycosylation patterns typical of those associated with the relevant host and/or with the altered alpha subunits. In addition, a mutant CHO cell line deficient in N-acetyl glucosaminyl-transferase I activity, such as 15B, can be used to alter glycosylation in both the alpha and beta subunits of FSH or other heterodimeric hormones.

Influence of Glycosylation on Secretion of Human Alpha Subunit

The resultant alpha subunit expression systems constructed as described in the paragraphs above were transfected into CHO cells using a modification of the calcium phosphate method wherein cells were selected for insertion of the plasmid DNA by growing in a culture medium containing 0.25 mg/ml of G418. Resistant colonies were harvested eleven days after transfection and screened for expression of alpha subunit by immunoprecipitation of media or lysates of the cells with the appropriate antiserum. The CHO cells were maintained in Ham's F12 medium supplemented with pen/strep and glutamine (2 mM) containing 5% v/v FCS at 37° C. in a humidified 5% $CO_2$ incubator; transfected clones were maintained with the addition of 0.125 mg/ml G418.

For metabolic labeling, on day 0 the cells were placed into 12 well dishes at 350,000 cells/well in 1 ml medium supplemented with 5% FCS. For continuous labeling experiments, the cells were washed twice with cysteine-free medium supplemented with 5% dialyzed calf serum in place of FCS and were labeled for 7–8 hr in 1 ml of cysteine-free medium containing 5% dialyzed calf serum and 50 uCi/ml $^{35}$S-cysteine (more than 1,000 Ci/mmol). The cell lysates or media were then immunoprecipitated and, if appropriate, treated with endoglycosidases as described by Corless, C. L. et al. *J Cell Biol* (1987) 104:1173–1181. The immunoprecipitates were resolved on 15% SDS polyacrylamide gels.

Using this analysis method, it was clear that the level of glycosylation had an influence not only on the secretion of the alpha subunit, but also on its processing. The results are summarized in Table 1:

TABLE 1

|  | Lysate | Medium | % Secreted |
|---|---|---|---|
| αWT | 23 kd | 28 kd | >95% |
| αΔAsn1 or αΔThr1 | 20 kd | 22 kd | >95% |
| αΔAsn2 or αΔThr2 | 20 kd | 23.5 kd | <20% |
| αΔAsn(1 + 2) or αΔThr(1+2) | 15 kd | 15 kd | 50% |
| αWT + tunicamycin | 15 kd | 15 kd | >95% |

As shown in Table 1, loss of the glycosylation at the position 78 Asn glycosylation site resulted in a substantial decrease in the efficiency of secretion. Evidently additional glycosylation takes place during the secretion event as evident by the higher molecular weight found in the medium. This was confirmed by treatment of the secreted forms with endoglycosidaseF which cleaves complex oligosaccharides in addition to high mannose noncomplex and hybrid-type oligosaccharides. More than 95% of the secreted material is sensitive to endoglycosidaseF, but not to endoglycosidaseH which cleaves only high mannose noncomplex and hybrid-type oligosaccharides.

Pulse chase experiments performed as described in Matzuk, M. M. et al. *J Cell Biol* (1988) 106:1049–1059, incorporated herein by reference, shows that the somewhat lower levels of secreted αΔAsn1 or αΔThr1 is due to clonal variation rather than differences in secretion or degradation rates. However, the mutants lacking glycosylation at the second (position 78) glycosylation site showed decreased secretion rates and an increased degradation rate.

It is clear from these results that the glycosylation at position 2 has a profound influence both on secretion rate and on the intracellular stability of the alpha subunit alone.

Influence of Alpha Subunit Glycosylation on Secretion of hCG

The influence of the glycosylation state of the alpha subunit on the efficiency of assembly of the dimeric hormone hCG was also studied in Matzuk, M. M. (supra).

In the clones wherein hCG beta is formed in excess of the alpha subunit, all of the wild type alpha subunit is mobilized into the dimeric form of the hormone for secretion. On the other hand, those mutants which are missing oligosaccharide from position 52 (glycosylation site 1) are deficient in the secretion of intact hCG dimer by virtue of altering the assembly and/or stability of the dimer complex. However, loss of glycosylation at position 2 seems to have no effect on assembly of the dimeric hormone. Removal of both glycosylation sites has an intermediate effect on assembly; the removal of glycosylation from both sites seems to have a lesser effect on the ability of the hormone to assemble than removal of the glycosylation from position 1 alone. In addition, the beta subunit of hCG stabilizes the mutants at position 2 from degradation of the alpha subunit.

It is clear from the foregoing results that the glycosylation pattern of the alpha subunit determines both the ability of the alpha subunit itself to be secreted and its ability to dimerize with the beta subunit to form intact hormone.

As noted in the paragraph describing the production of alpha subunit muteins, certain designated amino acids in the carboxy-terminal portion of the alpha subunit are required for signal transduction activity. Accordingly, inactivated alpha subunit is useful in the construction of antagonists by dimerization with the appropriate beta subunit of any of the hormones FSH, LH, CG and TSH.

In addition, it has been shown that FSH produced in CHO cells deficient in the glycosylation enzyme N-acetyl-glucosamine transferase-1 (NAGT-) results in an Asn-linked (GLcNAc)$_2$ (mannose)$_5$ oligosaccharides. Production of FSH in CHO cells lacking CMP-sialic acid transport into the Golgi apparatus (ST$^-$) results in sialic acid deficient FSH.

However, it is clear that the influence of the glycoprotein alpha subunit on secretion of beta subunits of the four hormones in this group differs depending on the nature of the beta subunit. Matzuk, M. M., et al. *Molec Endocrinol* (1988) 2:95–100, incorporated herein by reference, show that the presence of the alpha glycoprotein has a different effect on the secretion of human thyrotropin as opposed to human CG or LH. It has been shown that in the absence of the alpha subunit, CG beta is efficiently secreted, but TSH and LH beta subunits are slowly degraded intracellularly and less than 10% secreted into the medium. However, in the presence of the alpha subunit, CG beta is also secreted efficiently as the intact dimeric hormone while only 50% of LH beta appears in the medium as LH dimer. On the other hand, the alpha subunit efficiently combines with TSH beta, since greater than 95% of this beta subunit was secreted as the dimer. This demonstrates that the assembly of the dimeric hormone is dependent on the nature of both subunits.

As described in the paragraphs with regard to the construction of expression systems for FSH beta, mutein forms of FSH beta which are superior in circulating half-life can be produced by construction of a mutein containing the CTP amino acid sequence at the carboxy terminus of human CG beta. In addition, the N-linked glycosylation sites of the FSH beta subunit can be deleted or altered without affecting receptor binding activity.

Mutein forms of hCG are also included in the scope of the invention. Various muteins of hCG containing deleted or altered N-linked glycosylation sites are recombinantly produced by construction of expression systems analogous to those for FSH beta and for the alpha subunit from the suitably modified forms of the appropriate genes. Absence of any or all of the hCG N-linked oligosaccharides had only a minor effect on receptor affinity; with respect to the production of cAMP and steroidogenesis, absence of N-linked oligosaccharides from CG beta or from Asn-78 of the alpha subunit had no effect. However, the oligosaccharide at asparagine-52 of alpha was critical for cAMP and steroid production. In addition, its absence unmasked differences in the two N-linked oligosaccharides present in CG beta and inhibited in vitro biological activity.

What is claimed is:

1. A DNA molecule comprising a recombinant expression system capable, when transformed into a recombinant host cell, of expressing a gene encoding a mutein of the human gonadotropin alpha subunit which mutein, when combined with a beta gonadotropin subunit results in a modified gonadotropin hormone which is an antagonist to the corresponding native gonadotropin hormone    which expression system comprises an oligonucleotide sequence encoding a human alpha subunit mutein lacking through deletion or alteration one or more of amino acids 88–92 of the native subunit operably linked to control sequences functional in said host cell.

2. The DNA molecule of claim 1 wherein said control sequences comprise a promoter functional in mammalian cells.

3. Recombinant host cells modified to contain the DNA molecule of claim 1.

4. The cells of claim 3 which are Chinese hamster ovary (CHO) cell mutants deficient in N-acetyl glucosaminyl transferase-I activity.

5. The cells of claim 4 which are CHO-15B mutants.

6. The DNA molecule of claim 1 wherein said human alpha subunit mutein further lacks a glycosylation site at position 52 or 78 or both.

7. Recombinant host cells modified to contain the DNA molecule of claim 6.

* * * * *